United States Patent [19]

Pomper et al.

[11] Patent Number: 4,652,453
[45] Date of Patent: Mar. 24, 1987

[54] PREPARATION OF FREE-FLOWING PARTICULATE YEAST

[75] Inventors: Seymour Pomper, Stamford, Conn.; Edward V. Moore, Beacon, N.Y.

[73] Assignee: Nabisco Brands, Inc., Parsippany, N.J.

[21] Appl. No.: 579,099

[22] Filed: Feb. 10, 1984

[51] Int. Cl.$^4$ ................................................. A23C 1/28
[52] U.S. Cl. ........................................ 426/62; 426/656
[58] Field of Search ...................... 426/26, 60, 19, 62, 426/656; 435/256

[56] References Cited

U.S. PATENT DOCUMENTS 3,407,072 10/1968 Aizawa et al. ........................ 426/62
4,160,040 7/1979 Luca et al. ............................ 426/62
4,232,045 11/1980 Pomper et al. ....................... 426/19

OTHER PUBLICATIONS

The Condensed Chemical Dictionary, 7th Ed., 1969, Reinhold Book Corp., N.Y., pp. 169 and 577.

Primary Examiner—Sam Rosen
Assistant Examiner—William J. Herald
Attorney, Agent, or Firm—Richard Kornutik

[57] ABSTRACT

Baker's yeast, having a moisture content of from about 65 to about 75 percent by weight, is provided in a free-flowing particulate form by dispersing throughout a particulate baker's yeast, having a moisture content of from about 65 to 75 percent by weight, a small but effective amount of a finely-divided insoluble salt of an alkaline earth metal, particularly calcium sterate, magnesium sterate, tricalcium phosphate, or mixtures thereof without added acid. The resultant baker's yeast exhibits increased flowability and is retained in free-flowing particulate form for extended periods of time under a variety of conditions. As compared to baker's yeast which has not been treated with the alkaline earth metal salt, the treated baker's yeast exhibits no loss in leavening activity.

11 Claims, No Drawings

PREPARATION OF FREE-FLOWING PARTICULATE YEAST

BACKGROUND OF THE INVENTION

The present invention relates to baker's yeast and, more particularly, to the provision of a free-flowing particulate baker's yeast having a moisture content in the range of from about 65 to 75 percent by weight.

Yeast which is used for baking purposes generally is produced and sold in two distinct forms, i.e., as fresh yeast having a moisture content of from about 65 to 75 percent by weight (which typically is the range of moisture which is obtained from standard mechanical dehydration (centrifugation/filtering) of cream yeast resulting from the propagation of yeast in commercial-scale fermentors), and as active dried yeast, having a moisture content generally below about 10 percent by weight (achieved by evaporative drying under controlled conditions).

Fresh baker's yeast is a popular form in which yeast is used in both commercial and home baking, and is provided for this purpose either in compressed form or in a "bulk" form in which the yeast is granular. Bulk yeast finds significant application in commercial baking operations in which continuous or semi-continuous metering of ingredients is required.

Owing to the high moisture content of bulk yeast, its maintenance in the required particulate, free-flowing form often presents difficulties. The bulk yeast comprises a mass of living yeast cells having varying amounts of extracellular water in the interstitial spaces between and surrounding the cells. Water also is a major component of the yeast cells per se (commonly referred to as internal or intracellular water), and the relative amounts of water inside of and external to the cells are largely governed by equilibrium considerations. In general, the greater the proportion of extracellular water, the wetter the consistency of the bulk yeast and the greater the tendency of the yeast to coalesce and become less free-flowing. The problems in establishing and maintaining free-flowability of bulk yeast become particularly aggravated with increasing storage time and with storage conditions in which temperature extremes are encountered.

Workers in the art have suggested a number of techniques for improving the flow characteristics of bulk yeast. One suggestion has been to dry the yeast to a lower moisture content, e.g., below about 65 percent by weight. While perhaps effective in establishing and maintaining good flow characteristics, this method adds considerably to the cost of granular yeast since it requires additional energy and labor. Moreover, for yeast manufacturing facilities in which a variety of yeast products are produced (e.g., both compressed yeast and bulk yeast), it often is impractical and disadvantageous to attempt to establish different dewatering and/or drying facilities and conditions for these products.

Other approaches to this problem involve the addition of various materials to the bulk yeast. For example, British Patent Specification No. 1,397,410 discloses a mixture of granulated yeast (either "moist" yeast having a dry matter content of from 27 to 45 percent by weight or "dried" yeast having a dry matter content of greater than 92 percent by weight) and from about 0.5 to 3.0 percent by weight (dry basis) of hydrophobic silicic acid in order to aid flowability. U.S. Pat. No. 4,232,045 discloses the incorporation of small amounts of non-deliquescent drying agents such as hydrophilic silicon dioxide, micronized wood pulp or micronized cellulose to bind or absorb extracellular moisture in a bulk yeast so as to maintain flowability over extended time periods. British Patent Specification No. 1,560,478 discloses the addition of from 0.5 to 25 percent by weight of a "solid, highly water-absorbing agent" to a granulated compressed yeast for the same purpose.

German Offenlegungsschrift No. 2651349 discloses the use of a combination of both a hydrophilic agent and a hydrophobic agent to improve the "shelf-life" and "pourability" of fresh baker's yeast. Particular examples in this publication describe the use of combinations of hydrophilic silica and hydrophobic silica and a combination of hydrophobic silica and a swelling starch. The published application also suggests the use of salts of higher fatty acids, such as magnesium stearate, as hydrophobic substances which can be employed along with a hydrophilic substance. However, it is disclosed that when such salts are employed, an organic acid also must be used in order to neutralize the "alkalizing action" of these salts.

Attainment of free-flowing bulk yeast through use of additives is a desirable goal and inherently less capital- and labor-intensive than resort to techniques which involve additional drying of the bulk yeast. However, utilization of additives necessarily requires concern for the compatability of the additives with yeast and the products in which the yeast is employed, as well as the effect of the additives on the ultimate functional properties of the yeast in baking. From simply a generalized economic and functional viewpoint, it is highly desirable that the additive be effective for its intended purposes at low levels and that use of the additive require neither special processing considerations nor use of a necessary co-additive (e.g., the previously disclosed need for use of an organic acid in systems where a combination of hydrophilic agent and a hydrophobic metal salt of a higher fatty acid is used). Similarly, from an aesthetic point of view, any additive(s) employed must not impart undesired colors, flavors, textures or aromas to the yeast or the products in which the yeast is to be used.

Study of the use of additives to establish and maintain free-flowing characteristics in bulk yeast indicates that broad generalizations with respect to anticipated functionality are of little value. For example, although the art broadly discloses the use of strongly water-absorbing agents to promote free-flow characteristics of bulk yeast, numerous additives falling within this class either fail in this purpose or produce bulk yeast products which, while free-flowing, exhibit reduced leavening activity as compared to an untreated bulk yeast. The same is true for a number of hydrophobic agents, whether used alone or in combination with other additives.

SUMMARY OF THE INVENTION

It is an object of the present invention to provide a particulate, free-flowing bulk yeast which maintains its free-flow properties for extended periods of time at various storage and use conditions, and which exhibits these properties without adverse effect on its leavening properties.

This and other objects are achieved by the provision of a particulate baker's yeast, having a moisture content of from about 65 to 75 percent by weight, in which there has been incorporated an amount of a finely-divided insoluble salt of an alkaline earth metal effective to provide a free-flowing character to the particulate yeast which is maintained for extended periods of time under a variety of storage conditions. Most importantly, the insoluble salts for use in the present invention are effective for this purpose at low levels of addition (for example, in the range of from about 0.2 to about 3.0 percent by weight of the yeast) and do not adversely affect the leavening properties of the yeast.

The particular alkaline earth metal salt must of course be non-toxic both as to the yeast in which it is employed as well as to the ultimate consumers of products containing the yeast. In practical effect, based upon current knowledge and technology, this will require that the alkaline earth metal be selected from calcium, magnesium or mixtures thereof, and the salts of such metals constitute the preferred additives of the present invention.

Although any insoluble calcium or magnesium salt may be employed in accordance with the present invention, preferred salts are selected from the stearates of calcium and magnesium and tricalcium phosphate. Contrary to suggestions made by prior workers in this field, it has been found that these insoluble calcium or magnesium salts, which are essentially hydrophobic, are effective in promoting free-flowability to bulk yeast, without adverse effect on the leavening activity of the yeast, without the need for the additional presence of a hydrophilic material. Moreover, in the case where calcium or magnesium salts of higher fatty acids are employed as the insoluble salts, it is not required that an acid be employed as a co-additive. Indeed, the presence of such acid adversely affects the leavening activity of the yeast.

DETAILED DESCRIPTION OF THE INVENTION

In accordance with the preferred embodiment of the present invention, a baker's yeast, having a moisture content of from about 65 to 75 percent by weight, is treated with from about 0.2 to about 3.0 percent by weight of a finely-divided insoluble salt of either calcium or magnesium. Mixtures of insoluble salts of calcium and magnesium, having a total weight percent within the same 0.2 to 3.0 percent range, also may be employed.

Typically, the yeast will first itself be granulated prior to addition of the insoluble calcium or magnesium salt. Granulation may be effected by any suitable means such as grinding, pulverizing, screening or the like, and will preferably be such as to obtain an average particle size for the yeast of about 0.25 inches (diameter) or less, and preferably from about 0.04 to about 0.15 inches (diameter). It is possible however, to first incorporate the insoluble calcium or magnesium salt in yeast of larger particle size and thereafter subject the treated yeast to a granulation process.

The moisture content of the yeast, both before and after addition of the insoluble calcium or magnesium salt thereto, is in the range of from about 65 to 75 percent by weight. Preferably, the moisture content of the yeast will be in the range of 65 to 70 percent by weight and, most preferably, on the order of from about 68 to 69 percent by weight. The addition of the small amounts of the calcium or magnesium salts required by the present invention effects no drying as such in the bulk yeast.

At the time of addition of the insoluble calcium or magnesium salt to the yeast, the salt is in a finely-divided form, typically at a particle size less than about 100 m$\mu$, and most preferably in the range of from about 10 to 30 m$\mu$. The salt may be added to the yeast in any convenient manner, such as by metering the finely-divided salt into the yeast from a dispenser disposed above a screw conveyor along which the yeast is transported in typical commercial operations. Other methods of addition designed to achieve thorough dispersion of the finely-divided salts throughout the yeast also may be employed, such as shaking a mixture of the yeast and salt in a suitable vessel.

As earlier noted, the amount of finely-divided insoluble calcium and/or magnesium salt which is added to the bulk yeast is that which is effective to provide free-flow properties of the yeast. Typically, this will require an amount of salt(s) within the range of from about 0.2 to about 3.0 percent by weight of the yeast, and preferably will be from about 0.2 to about 1.0 percent by weight. A most preferred level of addition will be from about 0.4 to about 0.8 percent by weight of the yeast.

The insoluble calcium and/or magnesium salt for use in the present invention may be any such salt which is suitable for food use and which is substantially hydrophobic, i.e., will absorb moisture to a degree of less than about 10 percent of its weight when exposed to water-saturated air in a constant humidity chamber over a period of seven (7) days. Various insoluble carbonates, phosphates, stearates or the like may be employed having these properties. Most preferred are calcium stearate, magnesium stearate and calcium (tribasic) phosphate or mixtures of these salts.

Surprisingly, it has been found that the attainment of the required effects of promoting free-flow characteristics and not affecting the leavening properties of the yeast is not a function simply of the hydrophobic or hydrophilic nature of the additive or the particular cation or anion employed. For example, aluminum stearate, as compared to magnesium and calcium stearate at similar test conditions, is a poor promoter of free-flowability. Zinc stearate, while effective in maintaining free-flow properties in bulk yeast, significantly and deleteriously affects the leavening activity of the yeast.

The foregoing effects are demonstrated in examples and data presented hereinafter. In these examples, the flowability of the treated bulk yeast under a variety of conditions is quantified in terms of the "angle of repose" assumed by the yeast when subjected to the following procedure. A cylinder, open at both ends and about 2.5 inches in height and having an internal diameter of 2.0 inches, is placed on a flat surface and filled to the top with the particulate bulk yeast (treated or untreated according to the invention as the case may be). The cylinder is then raised from the flat surface and the yeast falls onto the surface. The dimensions of the cone formed by the faling yeast on the flat surface can be correlated to flowability by determining the angle of repose (A) as follows:

$$A = \tan^{-1} h/(d/2)$$

where d is the diameter of the cone and h the height of the cone. The lower the angle of repose, the greater the free-flowing character of the yeast.

As earlier noted, freshly prepared bulk yeast, untreated according to the invention, generally will exhibit satisfactory free-flow characteristics, although improvement can be obtained using the additives of the present invention. Over time, however, and particularly under storage conditions often encountered in commercial environments, the free-flow character of untreated bulk yeast decreases drastically. The free-flow characteristics obtained with particulate yeast treated according to the present invention will generally be as follows, using an average yeast particle size of about 0.05 inches:

After storage for four (4) days at 86° F., angle of repose less than about 50;

After storage for seven (7) days at 77° F., angle of repose less than about 50; and After freezing (24 hours) followed by seven (7) days storage at 77° F., angle of repose less than about 60.

The effects of the additives on the leavening activity of the yeast are determined by measurement of carbon dioxide production in simulated fermentation tests. In these tests, a standardized quantity of a particular yeast is incorporated in a standardized ingredient formulation (e.g., a high sugar dough, a no sugar dough, a sponge dough or a no flour "brew" formulation) and then capped in a sealed bottle connected to a gas collecting burette. The quantity of gas evolved in a fixed time period (2½ hours in the tests here presented) is then determined (corrected in each case to 760 mm Hg and 25° C.) and compared to values determined in similar tests using yeast of equivalent freshness, treated or untreated, as the case may be, in accordance with the invention.

EXAMPLE I

In this example, data obtained in testing bulk yeast either untreated or treated with various additives is presented.

Separate portions of bulk yeast having a moisture content of 68.5 percent by weight and an average particle size diameter of 0.05 inches were treated with the salts shown below at a level of 0.8 percent of the salt by weight of the yeast. The particle size of the various salts was on the order of about 30 mµ. The samples were prepared by combining the yeast and the salt in mason jars and shaking the jars thirty (30) times to distribute the additive throughout the yeast. In Table I the results of angle of repose measurements under the storage conditions indicated are presented.

TABLE I

| Additive | Angle of Repose | | | |
|---|---|---|---|---|
| | Fresh | 4 days @ 86° F. | 7 days @ 77° F. | Freezing + 7 days @ 77° F. |
| Untreated | 23.4 | No Flow | No Flow | No Flow |
| Mg stearate | 20.2 | 46.5 | 46.0 | 56.0 |
| Ca stearate | 15.0 | 32.1 | 30.6 | 42.2 |
| Zn stearate | 23.5 | 34.5 | 29.0 | 45.0 |
| Al stearate | 17.4 | No Flow | No Flow | No Flow |

The effect of the additives on the leavening activity of the yeast is shown in Table II (cubic centimeters of gas evolved—corrected to 760 mm Hg and 25° C.—over 2½ hours) for a number of ingredient formulations. As used in this and the previous table, "fresh" yeast (which was used in the test unless otherwise indicated) was a commercially prepared bulk yeast obtained from a normal plant production which was refrigerated at 40° F. for about one week from the time of production to the time of testing. All other time periods reflect additional days during which this fresh yeast was subjected to the various conditions.

All samples employed yeast having a moisture content of 68.5 percent, an average yeast particle size of 0.05 inch, an additive level (where used) of 0.8 percent by weight, and an additive particle size of 30 mµ.

TABLE II

| | Formulation | | | | |
|---|---|---|---|---|---|
| | High Sugar | | | | |
| Additive | Fresh | 3 days @ 77° F. | No Sugar | Sponge Dough | No Flour Brew |
| Untreated | 159 | 103 | 184 | 167 | 110 |
| Mg stearate | 161 | 121 | 179 | 172 | 106 |
| Ca stearate | 166 | 113 | 181 | 161 | 109 |
| Al stearate | 156 | 102 | 181 | 165 | 107 |
| Zn stearate | 123 | 86 | 135 | 169 | 101 |

In tests similar to those shown above, tricalcium phosphate, at levels of 0.5 percent and 1.0 percent by weight of the bulk yeast, was effective in improving the flowability of bulk yeast over extended periods of times without adverse effect on the leavening activity of the yeast.

Although the invention has been described with reference to particular embodiments and examples, these have been presented for illustrative purposes only and are not intended to limit the scope of the invention as defined by the appended claims. Many variations and modifications within the scope and spirit of the claim invention will be apparent to those of skill in this art.

What is claimed is:

1. A process for preparing a particulate baker's yeast, having a moisture content of from about 65 to 75 percent by weight, comprising the steps of (a) incorporating into a particulate baker's yeast, having a moisture content of from about 65 to 75 percent by weight, an amount of an additive consisting essentially of an essentially hydrophobic, finely-divided, insoluble salt of an alkaline earth metal selected from the group consisting of calcium stearate, magnesium stearate, tricalcium phosphate, and mixtures thereof effective to maintain the particulate yeast free-flowing under normally encountered conditions of commercial storage without adversely affecting the leavening activity of the yeast as compared to the same particulate baker's yeast not containing said additive material, and (b) maintaining the moisture content of said admixture of particular baker's yeast and said additive material within the range of from about 65 to 75 percent by weight, wherein said admixture of particulate baker's yeast and said additive material contains no added hydrophilic material and no added acid.

2. A process according to claim 1 wherein the amount of said additive is in the range of from about 0.2 to about 3.0 percent by weight of the yeast.

3. A process according to claim 2 wherein the amount of said additive is in the range of from about 0.2 to about 1.0 percent by weight of the yeast.

4. A process according to claim 1 wherein the moisture content of said particulate baker's yeast into which said additive material is incorporated and the moisture content of the admixture of particulate baker's yeast and additive material is from about 65 to 70 percent by weight.

5. A process according to claim 1 wherein the particle size of said finely-divided material is less than about 100 mµ.

6. A process according to claim 5 wherein the particle size diameter of said particulate yeast is less than about 0.25 inches.

7. A process for preparing a baker's yeast, having a moisture content of from about 65 to 75 percent by weight, and free of added acid and added hydrophilic material, comprising the steps of (a) admixing with a particulate baker's yeast, having a moisture content of from about 65 to 75 percent by weight, an amount of an additive consisting essentially of an essentially hydrophobic, finely-divided, insoluble salt of an alkaline earth metal selected from the group consisting of calcium stearate, magnesium stearate, tricalcium phosphate, and mixtures thereof effective to maintain the particulate yeast free-flowing under normally encountered conditions of commercial storage without adversely affecting the leavening activity of the yeast as compared to the same particulate baker's yeast not containing said additive; and (b) maintaining the moisture content of said admixture of particulate baker's yeast and said additive within the range of from about 65 to 75 percent by weight, whereby the free-flowing character of the particulate yeast, based on a yeast particle size diameter of 0.05 inches, provides the following angles of repose under the following storage conditions:

Angle of repose less than about 50 for storage of four (4) days at 86° F.;

Angle of repose less than about 50 for storage of seven (7) days at 77° F.; and

Angle of repose less than about 60 for storage of seven (7) days at 77° F. after one (1) day at freezing conditions.

8. A particulate baker's yeast having a moisture content of from about 65 to 75 percent by weight and containing an additive consisting essentially of an essentially hydrophobic, finely-divided material selected from the group consisting of calcium stearate, magnesium stearate, tricalcium phosphate and mixtures thereof, the amount of said additive being effective to maintain the particulate yeast free-flowing under normally encountered conditions of commercial storage without adversely affecting the leavening activity of the yeast, said baker's yeast containing no added hydrophilic material and no added acid.

9. A particulate yeast according to claim 5 having a moisture content of from about 65 to 70 percent by weight.

10. A particulate yeast according to claim 8 wherein the amount of said additive is in the range of from about 0.2 to 1. percent by weight of the yeast.

11. A particulate yeast according to claim 8 wherein the average particle size diameter of said particulate yeast is less than about 0.25 inches.

* * * * *